(12) United States Patent
Perry et al.

(10) Patent No.: US 7,919,045 B2
(45) Date of Patent: *Apr. 5, 2011

(54) AUTO-CALIBRATION LABEL AND METHODS OF FORMING THE SAME

(75) Inventors: Joseph E. Perry, Osceloa, IN (US); Dijia Huang, Granger, IN (US); Steven C. Charlton, Osceloa, IN (US); Andrew J. Edelbrock, Granger, IN (US); Russell J. Micinski, South Bend, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 698 days.

This patent is subject to a terminal disclaimer.

(21) Appl. No.: 11/918,828

(22) PCT Filed: Apr. 18, 2006

(86) PCT No.: PCT/US2006/014573
§ 371 (c)(1),
(2), (4) Date: Oct. 18, 2007

(87) PCT Pub. No.: WO2006/113721
PCT Pub. Date: Oct. 26, 2006

(65) Prior Publication Data
US 2009/0081082 A1    Mar. 26, 2009

Related U.S. Application Data

(60) Provisional application No. 60/672,633, filed on Apr. 19, 2005.

(51) Int. Cl.
*G01N 21/00* (2006.01)
(52) U.S. Cl. ............... 422/64; 422/62; 422/63; 422/65; 422/99; 422/100; 436/180

(58) Field of Classification Search .............. 422/63–65, 422/99–100; 436/180
See application file for complete search history.

(56) References Cited

U.S. PATENT DOCUMENTS
5,366,609 A    11/1994  White et al. ................. 204/403
(Continued)

FOREIGN PATENT DOCUMENTS
EP    0 840 122 A2    5/1998
(Continued)

OTHER PUBLICATIONS

Written Opinion corresponding to International Patent Application Serial No. PCT/US2006/014573, European Patent Office, dated Oct. 26, 2006, 5 pages.
(Continued)

*Primary Examiner* — Jyoti Nagpaul
(74) *Attorney, Agent, or Firm* — Nixon Peabody LLP

(57) ABSTRACT

An auto-calibration circuit or label is adapted to be used with different instruments. The auto-calibration circuit comprises a first plurality of electrical connections and at least one electrical connection. The first plurality of electrical connections is utilized by the different instruments to auto-calibrate. The first plurality of electrical connections includes a first plurality of contact areas. At least one electrical connection is utilized solely by the second instrument to auto-calibrate and includes at least one contact area. This electrical connection is distinct from the first plurality of electrical connections. The first plurality of electrical connections is routed directly from each of the first plurality of contact areas to a respective first or second common connection. The at least one electrical connection is routed directly from the at least one contact area to the respective first common connection, the second common connection or a no-contact area.

25 Claims, 6 Drawing Sheets

U.S. PATENT DOCUMENTS

| | | | |
|---|---|---|---|
| 5,575,403 A | 11/1996 | Charlton et al. | 221/31 |
| 5,597,532 A | 1/1997 | Connolly | 422/58 |
| 5,628,890 A | 5/1997 | Carter et al. | 204/403 |
| 5,630,986 A | 5/1997 | Charlton et al. | 422/64 |
| 5,700,695 A | 12/1997 | Yassinzadeh et al. | 436/180 |
| 5,856,195 A | 1/1999 | Charlton et al. | 436/50 |
| 6,102,872 A | 8/2000 | Doneen et al. | 600/582 |
| 6,531,040 B2 | 3/2003 | Musho et al. | 204/401 |
| 2009/0041625 A1* | 2/2009 | Perry et al. | 422/68.1 |

FOREIGN PATENT DOCUMENTS

| | | |
|---|---|---|
| EP | 1 174 716 A2 | 1/2002 |
| EP | 1 288 653 A1 | 3/2003 |
| EP | 1 398 631 A2 | 3/2004 |
| EP | 1398631 * | 3/2004 |
| EP | 1 431 758 A1 | 6/2004 |
| WO | WO 2004/113911 A1 | 12/2004 |
| WO | WO 2004/113915 A1 | 12/2004 |

OTHER PUBLICATIONS

International Search Report corresponding to International Patent Application Serial No. PCT/US2006/014573, European Patent Office, dated Oct. 26, 2006, 4 pages.

* cited by examiner

AUTO-CALIBRATION LABEL AND METHODS OF FORMING THE SAME

CROSS-REFERENCE TO RELATED APPLICATIONS

This application claims priority to Application No. 60/672,633 filed on Apr. 19, 2005, which is incorporated by reference in its entirety.

FIELD OF THE INVENTION

The present invention generally relates to an auto-calibration circuit or label and methods of forming the same. The auto-calibration circuits or labels are adapted to be used in calibrating instruments or meters that determine the concentration of an analyte (e.g., glucose) in a fluid.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, sensors are used to test a sample of blood.

A test sensor contains biosensing or reagent material that reacts with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested. This signal is supplied to the meter via contact areas located near the rear or contact end of the sensor and becomes the measured output.

Diagnostic systems, such as blood-glucose testing systems, typically calculate the actual glucose value based on a measured output and the known reactivity of the reagent-sensing element (test-sensor) used to perform the test. The reactivity or lot calibration information of the test sensor may be given to the user in several forms including a number or character that they enter into the instrument. One prior art method included using an element that is similar to a test sensor, but which was capable of being recognized as a calibration element by the instrument. The test element's information is read by the instrument or a memory element that is plugged into the instrument's microprocessor board for directly reading the test element.

These methods suffer from the disadvantage of relying on the user to enter the calibration information, which some users may not do. In this event, the test sensor may use the wrong calibration information and thus return an erroneous result. Improved systems use an auto-calibration circuit or label that is associated with the sensor package. The auto-calibration circuit or label is read automatically when the sensor package is placed in the meter and requires no user intervention.

The success of sensing instruments has lead to the development of improved sensing instruments and improved sensors. For example, existing sensing instruments analyze the sample for a predetermined length of time equal to approximately 30 seconds. New improved sensing instruments, however, are designed for much shorter analysis times (e.g., 5 seconds) and the calibration information for the test sensor measured at the 30 seconds analysis time is likely to be different from the calibration information relevant to shorter analysis time.

As new and improved instruments or meters are being developed and used by consumers, the older instruments or meters will still be used for an unknown period of time. If calibration codes adapted for characteristics of the new and improved instruments are used in older meters, test results may be inaccurate, which is undesirable. It would be desirable to provide a device and method that provides the lot calibration information of the test sensor to at least two instruments or meters in a reliable manner. It would also be desirable for this device to be as compact as possible as the label has to fit into the restricted space available on the sensor package.

SUMMARY OF THE INVENTION

According to one embodiment, an auto-calibration circuit or label is adapted to be used with a first instrument and a second instrument. The first instrument is different from the second instrument. The auto-calibration circuit or label comprises a first plurality of electrical connections and at least one electrical connection. The first plurality of electrical connections is adapted to be utilized by the first instrument to auto-calibrate and is adapted to be utilized by the second instrument to auto-calibrate. The first plurality of electrical connections includes a first plurality of contact areas. At least one electrical connection is adapted to be utilized solely by the second instrument to auto-calibrate. The at least one electrical connection includes at least one contact area. The at least one electrical connection is distinct from the first plurality of electrical connections. The first plurality of electrical connections is adapted to be routed directly from each of the first plurality of contact areas to a respective first common connection or a second common connection. The at least one electrical connection is adapted to be routed directly from the at least one contact area to the first common connection, the second common connection or a no-contact area.

According to one embodiment, a sensor package is adapted to be used in a first instrument adapted to determine an analyte concentration in a fluid sample and in a second instrument adapted to determine the analyte concentration in the fluid sample. The first instrument is different from the second instrument. The sensor package comprises at least one sensor and an auto-calibration circuit or label. The at least one sensor is adapted to receive the fluid sample and is operable with the first instrument and the second instrument. The auto-calibration circuit or label is adapted to be used with the first instrument and the second instrument. The auto-calibration circuit or label includes a first plurality of electrical connections and at least one electrical connection. The first plurality of electrical connections is adapted to be utilized by the first instrument to auto-calibrate and is adapted to be utilized by the second instrument to auto-calibrate. The first plurality of electrical connections includes a first plurality of contact areas. The at least one electrical connection is adapted to be utilized solely by the second instrument to auto-calibrate. The at least one electrical connection includes at least one contact area. The at least one electrical connection is distinct from the first plurality of electrical connections. The first plurality of electrical connections is adapted to be routed directly from each of the first plurality of contact areas to a respective first common connection or a second common connection. The at least one electrical connection is adapted to be routed directly from the at least one contact area to the first common connection, the second common connection or a no-contact area.

According to one embodiment, a system for determining an analyte concentration in a fluid sample comprises a test sensor, a processor, and an auto-calibration circuit or label. The test sensor is adapted to receive the fluid sample. The processor is responsive to the test sensor and adapted to perform a predefined test sequence for measuring a predefined parameter value. The auto-calibration circuit or label is coupled to the processor for providing first information and second information corresponding to the test sensor. The processor is adapted to read the first information and second information. The first or second information is utilized by the processor for a predefined test sequence. The second information is defined by a first plurality of electrical connections and at least one electrical connection. The second information is used by the second instrument to auto-calibrate. The first information is defined by the first plurality of electrical connections. The first information is used by the first instrument to auto-calibrate. The first plurality of electrical connections includes a first plurality of contact areas. The at least one electrical connection includes at least one second contact area. The first plurality of electrical connections is distinct from the at least one electrical connection. The first plurality of electrical connections is adapted to be routed directly from each of the first plurality of contact areas to a respective first common connection or a second common connection. The at least one electrical connection is adapted to be routed directly from the at least one contact area to the first common connection, the second common connection or a no-contact area.

According to one method, an auto-calibration circuit or label adapted to be used with a first instrument and a second instrument is formed. The first instrument is different from the second instrument and is adapted to determine an analyte concentration of a fluid sample. A first plurality of electrical connections is supplied and is adapted to be utilized by the first instrument to auto-calibrate and is adapted to be utilized by the second instrument to auto-calibrate. The first plurality of electrical connections includes a first plurality of contact areas. At least one electrical connection is supplied and is adapted to be utilized solely by the second instrument to auto-calibrate. The at least one electrical connection includes at least one contact area. The at least one electrical connection is distinct from the first plurality of electrical connections. The first plurality of electrical connections is adapted to be routed directly from each of the first plurality of contact areas to a respective first common connection or a second common connection. The at least one electrical connection is adapted to be routed directly from the at least one contact area to the first common connection, the second common connection or a no-contact area.

DETAILED DESCRIPTION OF ILLUSTRATED EMBODIMENTS

An instrument or meter in one embodiment uses a test sensor adapted to receive a fluid sample to be analyzed, and a processor adapted to perform a predefined test sequence for measuring a predefined parameter value. A memory is coupled to the processor for storing predefined parameter data values. Calibration information associated with the test sensor may be read by the processor before the fluid sample to be measured is received. Calibration information may be read by the processor after the fluid sample to be measured is received, but not after the concentration of the analyte has been determined. Calibration information is used in measuring the predefined parameter data value to compensate for different characteristics of test sensors, which will vary on a batch-to-batch basis. Variations of this process will be apparent to those of ordinary skill in the art from the teachings disclosed herein, including but not limited to, the drawings.

Figure 1:
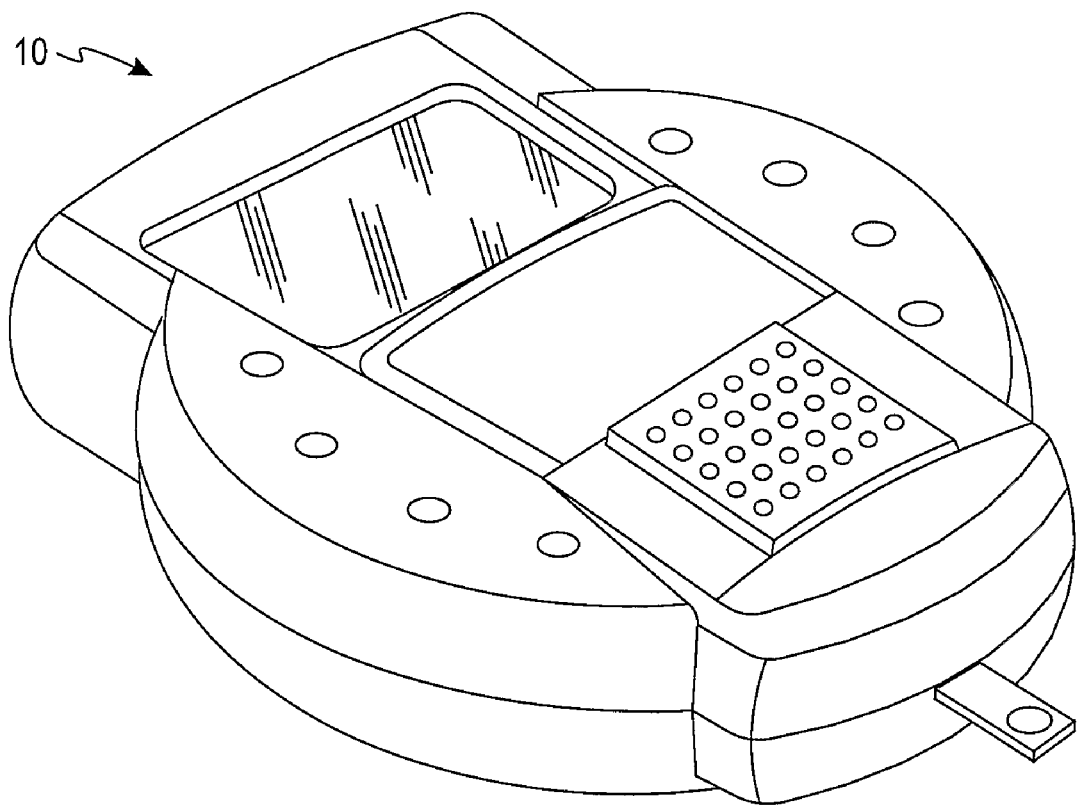
FIG. 1 shows a sensing instrument according to one embodiment.
Figure 2A:
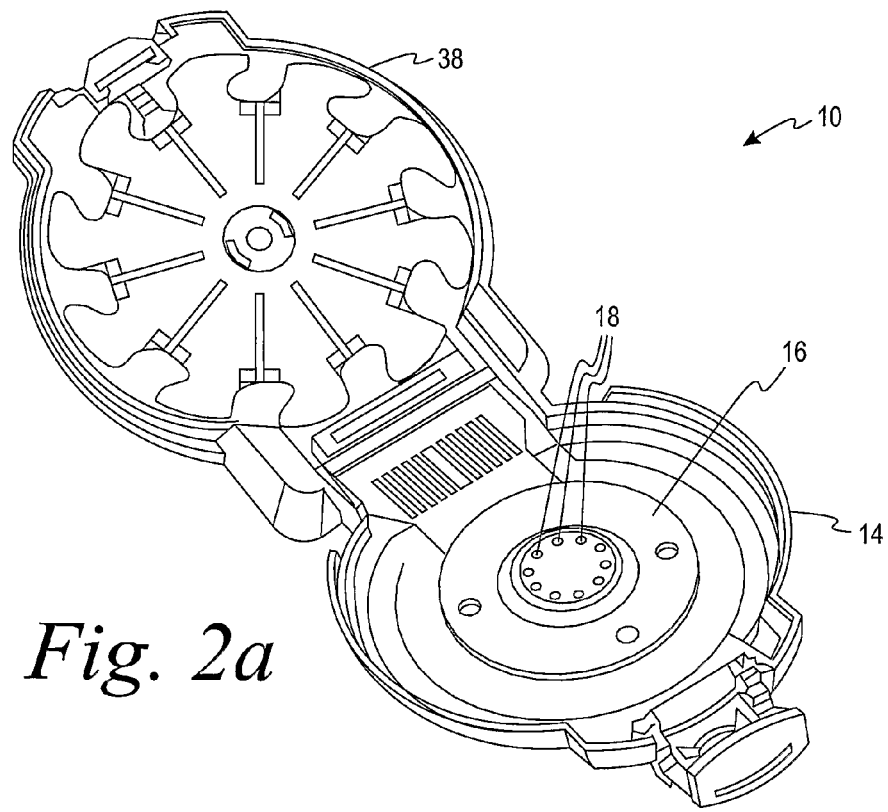
FIG. 2a shows the interior of the sensing instrument of FIG. 1.
Figure 2B:
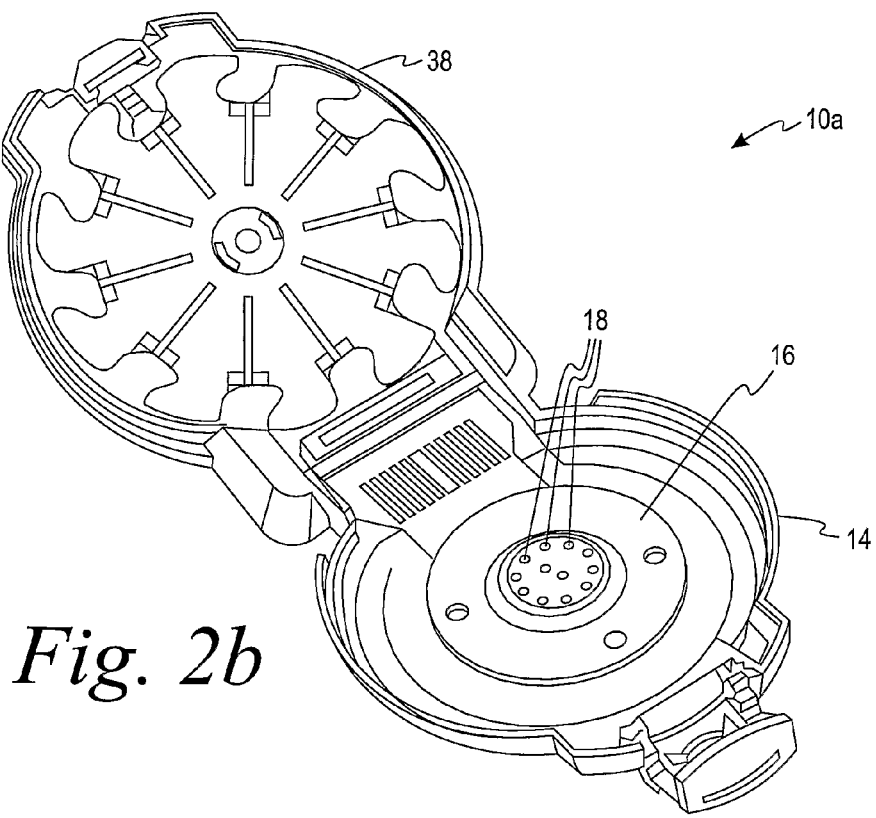
FIG. 2b shows the interior of a sensing instrument according to another embodiment.
Figure 3:
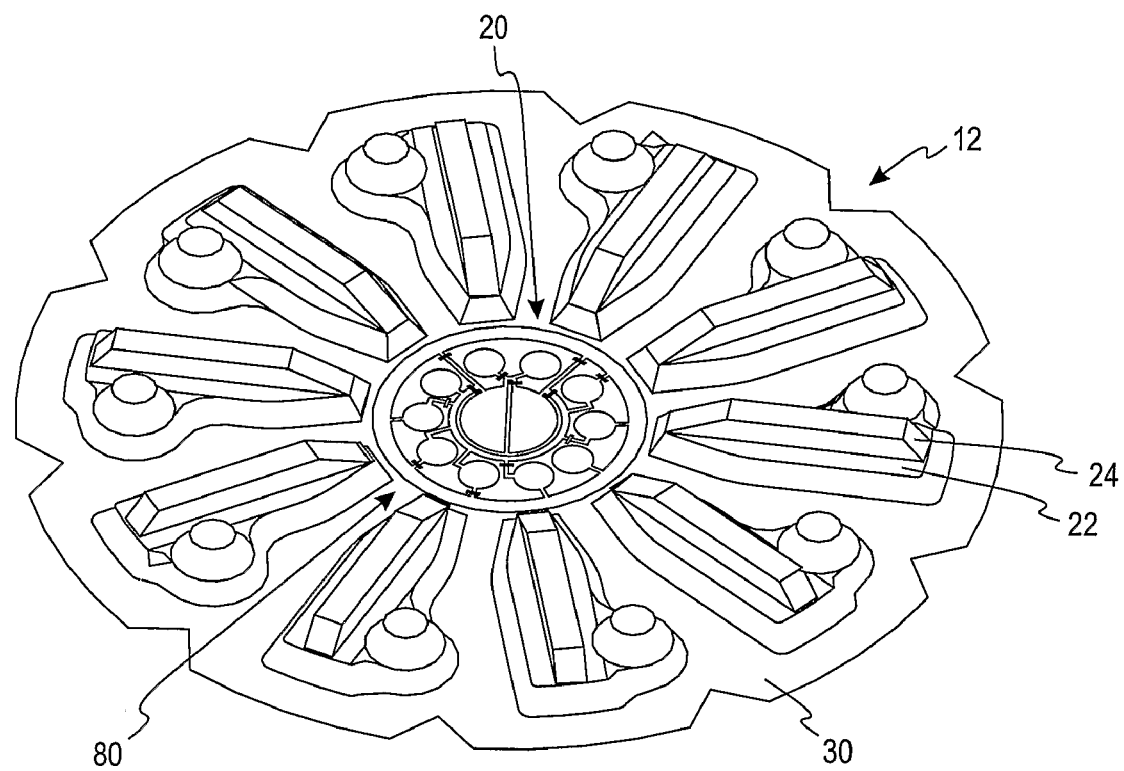
FIG. 3 shows a sensor package according to one embodiment for use with the sensing instrument of FIG. 2.

Referring now to FIGS. 1, 2a and 3, an instrument or meter 10 is illustrated. In FIG. 2a, the inside of the instrument 10 is shown in the absence of a sensor package. One example of a sensor package (sensor package 12) is separately illustrated in FIG. 3. Referring back to FIG. 2a, a base member 14 of the instrument 10 supports an auto-calibration plate 16 and a predetermined number of auto-calibration pins 18. As shown in FIG. 2a, for example, the instrument 10 includes ten auto-calibration pins 18. It is contemplated that the number of auto-calibration pins may vary in number and shape from that shown in FIG. 2a. For example, an instrument 10a is shown in FIG. 2b that includes twelve auto-calibration pins 18. The auto-calibration pins 18 are connected for engagement with the sensor package 12.

The sensor package 12 of FIG. 3 includes an auto-calibration circuit or label 20 and a plurality of test sensors 22. The plurality of test sensors 22 is used to determine concentrations of analytes. Analytes that may be measured include glucose, lipid profiles (e.g., cholesterol, triglycerides, LDL and HDL), microalbumin, hemoglobin $A_{1c}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

In one embodiment, the plurality of test sensors 22 includes an appropriately selected enzyme to react with the desired analyte or analytes to be tested. An enzyme that may be used to react with glucose is glucose oxidase. It is contemplated that other enzymes may be used such as glucose dehydrogenase. An example of a test sensor is disclosed in U.S. Pat. No. 6,531,040 assigned to Bayer Corporation. It is contemplated that other test sensors may be used.

Calibration information or codes assigned for use in the clinical value computations to compensate for manufacturing variations between sensor lots are encoded on the auto-calibration circuit or label 20. The auto-calibration circuit or label 20 is used to automate the process of transferring calibration information (e.g., the lot specific reagent calibration information for the plurality of test sensors 22) such that the sensors 22 may be used with different instruments or meters. The auto-calibration pins 18 electrically couple with the auto-calibration circuit or label 20 when a cover 38 of the instrument 10 is closed and the circuit or label 20 is present. The auto-calibration circuit or label 20 will be discussed in detail in connection with FIG. 4.

According to one method, an analyte concentration of a fluid sample is determined using electrical current readings and at least one equation. In this method, equation constants are identified using the calibration information or codes from the auto-calibration circuit or label 20. These constants may be identified by (a) using an algorithm to calculate the equation constants or (b) retrieving the equation constants from a lookup table for a particular predefined calibration code that is read from the auto-calibration circuit or label 20. The auto-calibration circuit or label 20 may be implemented by digital or analog techniques. In a digital implementation, the instrument assists in determining whether there is conductance along selected locations to determine the calibration information. In an analog implementation, the instrument assists in measuring the resistance along selected locations to determine the calibration information.

Referring back to FIG. 3, the plurality of test sensors 22 is arranged around the auto-calibration circuit or label 20 and extends radially from the area containing the circuit or label 20. The plurality of sensors 22 of FIG. 3 is stored in individual cavities or blisters 24 and read by associated sensor electronic circuitry before one of the plurality of test sensors 22 is used. The plurality of sensor cavities or blisters 24 extends toward a peripheral edge of the sensor package 12. In this embodiment, each sensor cavity 24 accommodates one of the plurality of test sensors 22.

The sensor package 12 of FIG. 3 is generally circular in shape with the sensor cavities 24 extending from near the outer peripheral edge toward and spaced apart from the center of the sensor package 12. It is contemplated, however, that the sensor package may be of different shapes then depicted in FIG. 3. For example, the sensor package may be a square, rectangle, other polygonal shapes, or non-polygonal shapes including oval.

Figure 4:
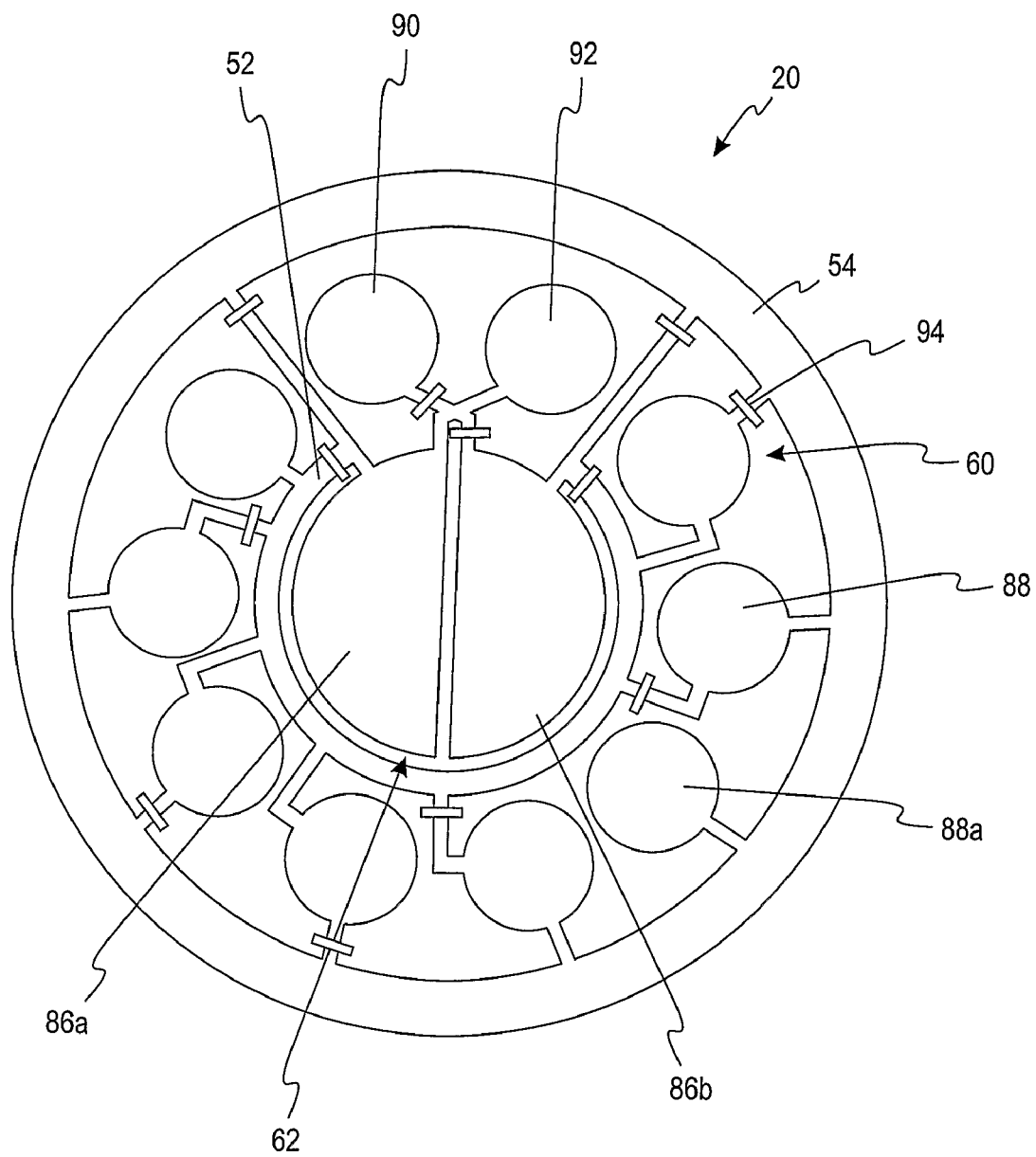
FIG. 4 shows an auto-calibration circuit or label according to one embodiment of the invention.

With reference to FIG. 4, the auto-calibration circuit or label 20 is adapted to be used with (a) the instrument or meter 10 (see FIG. 2a), (b) a second instrument or meter 10a (see FIG. 2b) being distinct or different from the instrument 10, and (c) the plurality of sensors 22 operable with both the instrument 10 and the second instrument 10a. Thus, the auto-calibration circuit or label 20 may be considered as "backwards" compatible because it is adapted to be used with the second instrument (i.e., a new instrument) and the first instrument (i.e., an older instrument). The auto-calibration label may be used to work with two older instruments or two newer instruments. To reduce or avoid manufacturing modifications, it is desirable for a "backwards" compatible auto-calibration label not to increase the size of the label or decrease the size of the electrical contact areas.

The sensor package 12 contains a plurality of sensors 22 operable with the instrument 10 and the second instrument. When the plurality of sensors 22 has essentially the same calibration characteristics, calibrating the instrument 10 for one of the sensors 22 is effective to calibrate the instrument 10 for each of the plurality of sensors 22 in that particular package 12.

The auto-calibration circuit or label 20 includes an inner ring 52, an outer ring 54, a plurality of electrical connections 60 and at least one electrical connection 62 distinct from the plurality of electrical connections 60. For some applications, the inner ring 52 represents logical 0s and the outer ring 54 represents logical 1s. It is contemplated that the inner ring or the outer ring may not be continuous. For example, the inner ring 52 is not continuous because it does not extend to form a complete circle. The outer ring 54, on the other hand, is continuous. The inner ring and the outer ring may both be continuous and in another embodiment the inner ring and the outer ring are not continuous. It is contemplated that the inner ring and outer rings may be shapes other than circular. Thus, the term "ring" as used herein includes non-continuous strictures and shapes other than circular.

The plurality of electrical connections 60 includes a plurality of outer contact areas 88 (e.g., contact pads). The plurality of outer contact areas 88 is radially positioned around the circumference of the auto-calibration circuit or label 20. The at least one electrical connection 62 includes a plurality of inner contacts areas 86a,b (e.g., contact pads). The inner contact areas 86a,b are positioned at the general center of the label 20. In this embodiment, conductive ink forms the plurality of inner contacts areas 86a,b and the plurality of outer contact areas 88 with no ink in the spaces therebetween.

It is contemplated that the at least one electrical connection may include exactly one inner contact area. It is also contemplated that the at least one electrical connection may be located in other positions such as being farther from the center of the auto-calibration label than the plurality of electrical connections such as will be discussed below in connection with FIG. 6.

The at least one electrical connection 62 is distinct from the plurality of electrical connections 60. It will be understood, however, that use of the term "distinct" in this context may only mean that the encoded information is distinct, but the decoded information is essentially the same. For example, the instrument 10 and the second instrument may have essentially the same calibration characteristics, but the second instrument includes contacts to couple with the at least one electrical connection 62.

The plurality of electrical connections 60 is adapted to be routed directly from each of the plurality of outer contact areas 88 to a respective first common connection (e.g., inner ring 52) or a second common connection (e.g., outer ring 54). Thus, the electrical connections of the plurality of outer contact areas 88 are not routed through any of the inner contact areas 86. By having such an arrangement, additional independent encoded-calibration information may be obtained using the same total number of inner and outer contact areas 86, 88 without increasing the size of the auto-calibration circuit or label 20. Additionally, potential undesirable electrical connections may occur if the electrical connections of outer contact areas (e.g., outer pads) are routed through inner contact areas (e.g., inner pads).

The plurality of electrical connections 60 is adapted to be utilized by the first instrument to auto-calibrate and is also adapted to be utilized by the second instrument to auto-calibrate. The at least one electrical connection 62, on the other hand, is adapted to be utilized solely by the second instrument to auto-calibrate. Thus, the positioning of the outer contact areas 88 and the inner contact areas 86a, 86b permits the circuit or label 20 to be read by instruments or meters that are capable of contacting (a) only the plurality of outer contact areas 88 or (b) both the plurality of outer contact areas 88 and the inner contact areas 86a, 86b.

The information from the plurality of electrical connections 60 corresponds to the plurality of test sensors 22. The information obtained from the combination of the plurality of electrical connections 60 and the at least one electrical connections 62 also corresponds with the plurality of test sensors 22.

According to one embodiment, substantially all of the plurality of outer contact areas 88 are initially electrically connected to the first common connection (e.g., inner ring 52) and the second common connection (e.g., outer ring 54). To program the auto-calibration label, the conductive ink is typically severed to break the electrical connection from the outer contact areas 88 to either the inner ring 52 or outer ring 54 so that an individual outer contact area 88 is only connected to one of the inner or outer rings 52, 54. By having the individual outer contact areas 88 only connected to the inner or outer ring 52, 54 assists in maintaining a reliable instrument since any "no connect" may be sensed by the instrument software. Thus, a defective auto-calibration label or bad connection from the instrument may be automatically sensed by the instrument software.

The instrument may include several responses to reading the auto-calibration label. For example, responses may be include the following codes: (1) correct read, (2) misread, (3) non-read, defective code, (4) non-read, missing label, and (5) read code out-of-bounds. A correct read indicates that the instrument or meter correctly read the calibration information. A misread indicates that the instrument did not correctly read the calibration information encoded in the label. In a misread, the label passed the integrity checks. A non-read, defective code indicates that the instrument senses that a label is present (continuity between two or more auto-calibration pins), but the label code fails one or more encoding rules (label integrity checks). A non-read, missing label indicates that the instrument does not sense the presence of a label (no continuity between any of the auto-calibration pins). A read code out-of-bounds indicates that the instrument senses an auto-calibration code, but the calibration information is not valid for that instrument.

One method for severing the conductive ink is to break the electrical connection by using a laser cut. It is contemplated that other methods of breaking the electrical connection may be used such as punching holes through the label. As shown in FIG. 4, a number of cuts 94 are shown on the auto-calibration circuit or label 20 in one particular pattern. It is contemplated that the cuts may be formed in other locations than depicted in FIG. 4. Other patterns may be formed by performing different cuts than shown in FIG. 4.

It is also contemplated that the cuts may be formed on the first conductive ink pattern layer according to other methods. It is also contemplated that conductive ink may be printed with the appropriate "gaps" such that breaking the electrical connection by, for example, laser cutting is unnecessary.

The cuts 94 are formed such that the plurality of outer contact areas 88 will be only directly electrically connected to either the outer ring 54 or the inner ring 52. Typically, at least one of the outer contact areas 88 will always be directly electrically connected to the outer ring 54 or the inner ring 52 in the absence of the cut 94. For example, in FIG. 4, outer contact area 88*a* is always directly electrically connected to the outer ring 54.

Similarly, after the cuts 94 are formed, the inner contact areas 86*a*, 86*b* will be only directly electrically connected to either the outer ring 54, the inner ring 52, no-contact area 90, no-contact area 92, or to each other (inner contact area 86*a* being directly electrically connected to inner contact area 86*b*). No-contact areas 90, 92 are referred to as no-contact areas because the first instrument cannot directly electrically connect to these areas. The second instrument, on the other hand, can directly electrically connect to the no-contact areas through the at least one electrical connection. As shown in FIG. 4, inner contact area 86*a* is directly electrically connected to the no-contact area 92.

In the embodiment of FIG. 4, the location and operability of the electrical connections are "backwards" compatible. By adding at least one electrical connection, the second instrument (i.e., a new instrument) can sense calibration information not available from the plurality of electrical connections 60. The way that the at least one electrical connection 62 is connected allows the second instrument to detect an adjustment for the calibration information being read from the plurality of electrical connections 60 available to the first instrument. Thus, auto-calibration labels with only the plurality of electrical connections 60 are read by the first and second instruments. When a new auto-calibration label is distributed that includes the plurality of electrical connections 60 and the at least one electrical connection 62 it can also be read by the first and second instruments. The second instrument, however, can read the information from the at least one electrical connection 62, while the first instrument cannot.

Figure 5:
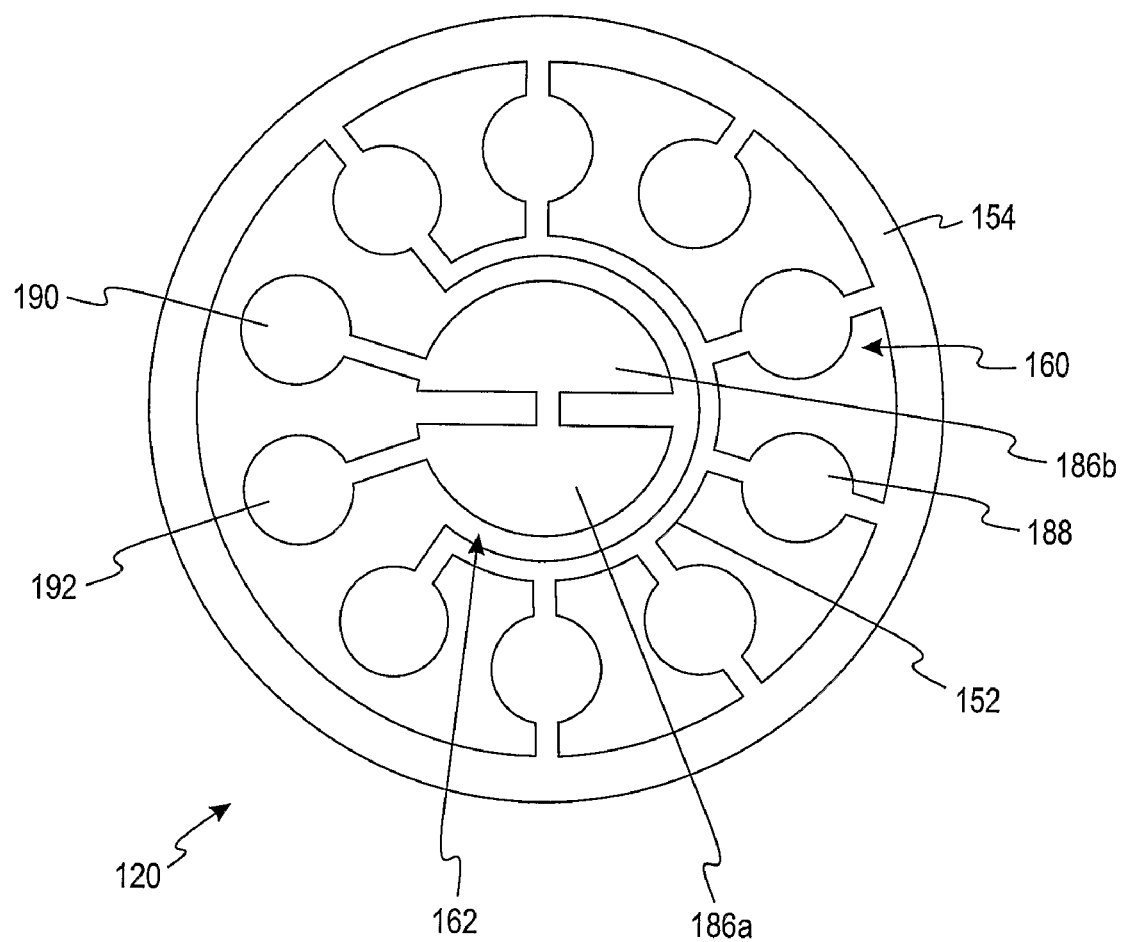
FIG. 5 shows an auto-calibration circuit or label according to another embodiment of the invention.

Another example of an auto-calibration circuit or label (auto-calibration circuit or label 120) is depicted in FIG. 5. Auto-calibration circuit or label 120 is similar to the auto-calibration circuit or label 20 depicted in FIG. 4. The auto-calibration circuit or label 120 includes a first common connection and a second common connection. Specifically, the auto-calibration circuit or label 120 includes an inner ring 152, an outer ring 154, a plurality of electrical connections 160, and at least one electrical connection 162. The plurality of electrical connections 160 includes a plurality of outer contact areas 188 (e.g., contact pads). The plurality of outer contact areas 188 is radially positioned around the circumference of the auto-calibration circuit or label 120. The at least one electrical connection 162 includes at least one inner contact area (e.g., a contact pad). As shown in FIG. 5, the at least one electrical connection 162 includes a plurality of inner contact areas 186*a*, 186*b*. The at least one electrical connection 162 is distinct from the plurality of electrical connections 160. The inner contact areas 186*a*, 186*b* may only be directly electrically connected to no-contact area 190, no-contact area 192, or each other. The auto-calibration circuit or label 120 is shown without cuts, but would include cuts or appropriate gaps such as shown, for example, with cuts 94 in connection with the auto-calibration label 20 in FIG. 4.

The auto-calibration circuits or labels 20, 120 of FIGS. 4, 5 are generally circular shaped. It is contemplated, however, that the auto-calibration circuit or labels may be of different shapes than depicted in FIGS. 4, 5. For example, the auto-calibration circuit or label may be a square, rectangle, other polygonal shapes, and non-polygonal shapes including oval.

It is also contemplated that the contacts areas may be in different locations than depicted in FIGS. 4, 5. For example, the contacts may be in a linear array. Also, it contemplated that the at least one electrical connection may be in different locations. For example, referring to FIG. 6, another example of an auto-calibration circuit or label (auto-calibration circuit or label 220). The auto-calibration circuit or label 220 includes a first common connection and a second common connection.

Figure 6:
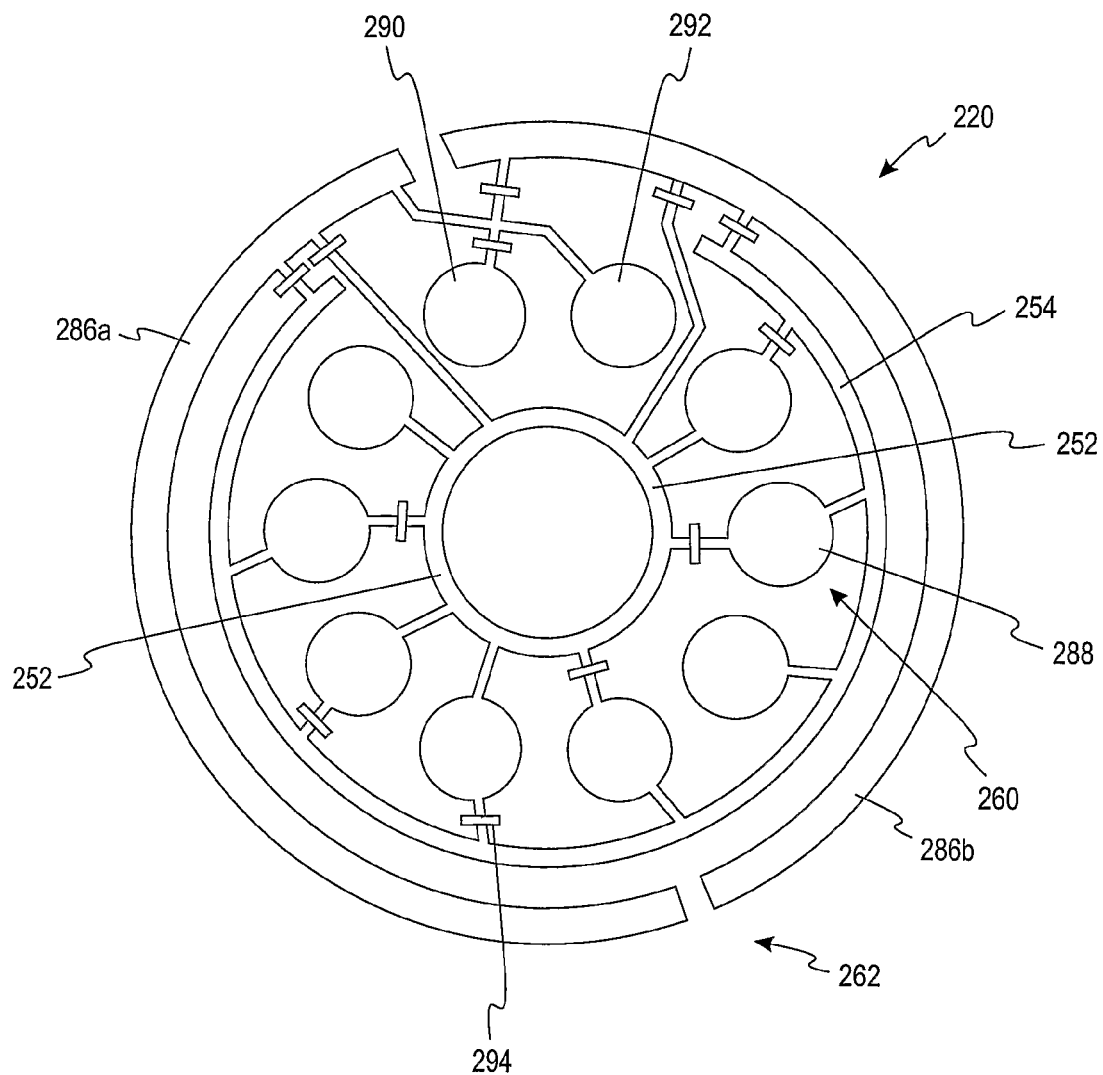
FIG. 6 shows an auto-calibration circuit or label according to a further embodiment of the invention.

Specifically, the auto-calibration circuit or label 220 includes an inner ring 252, an outer ring 254, a plurality of electrical connections 260, and at least one electrical connection 262. The inner ring 252 is a first common connection, while outer ring 254 is a second common connection. The plurality of electrical connections 260 includes a plurality of outer contact areas 288 (e.g., contact pads). The plurality of outer contact areas 288 is radially positioned around the circumference of the auto-calibration circuit or label 220. The at least one electrical connection 262 includes at least one outer contact area (e.g., a contact ring). As shown in FIG. 6, the at least one electrical connection 262 includes a plurality of outer periphery contact areas 286a, 286b. The at least one electrical connection 262 is distinct from the plurality of electrical connections 260. The outer periphery contact areas 286a, 286b may be directly electrically connected to no-contact area 290, no-contact area 292, inner ring 252, outer ring 254 or each other depending on the location of the cuts or gaps.

In one specific example, the auto-calibration circuit or label 220 of FIG. 6 includes selected cuts or gaps 294. In this embodiment, the periphery contact area 286a is directly connected to no-contact area 292, while periphery contact area 286b is not directly connected to any no-contact area or common connection. It is contemplated that other patterns may be formed with different cuts or gaps.

It is contemplated that the auto-calibration circuits or labels may be used with instruments other than instrument 10 depicted in FIGS. 1, 2. The auto-calibration circuits or labels may also be used in other type of sensor packs than sensor package 12. For example, the auto-calibration circuits or labels may be used in sensor packages such as a cartridge with a stacked plurality of test sensors or a drum-type sensor package.

According to one process, the auto-calibration circuits or labels are formed by printing such as by printing a single layer. The auto-calibration circuits or labels may be constructed by screenprinting conductive ink onto a base substrate, that may either be a separate substrate (not shown) or the sensor-package surface 30 of FIG. 3. A separate substrate may be attached to the sensor package 12 using, for example, an adhesive. Examples of adhesives include a hot melt, UV-cure or fast-curing adhesive. The auto-calibration circuits or labels are desirably a carbon, silver or a carbon/silver blended ink. The sensor-package surface 30 may be any print-receptive surface including paper, polymer-filled paper or polymer substrate (e.g., a heat-stabilized polyethylene terephthalate (PET) or polycarbonate).

It is contemplated that the auto-calibration circuits or labels 20, 120, 220 may be formed by other methods. For example, the auto-calibration labels may be formed using lasers. Non-limiting examples of lasers that may be used include solid-state lasers such as a yttrium-based laser, gas lasers such as a carbon dioxide-base laser, and Excimer lasers. The patterns formed on the labels by the lasers may be formed using a mask or by direct writing of the lines.

Alternative Embodiment A

An auto-calibration circuit or label adapted to be used with a first instrument and a second instrument, the first instrument being different from the second instrument, the auto-calibration circuit or label comprising:
  a first plurality of electrical connections being adapted to be utilized by the first instrument to auto-calibrate and being adapted to be utilized by the second instrument to auto-calibrate, the first plurality of electrical connections including a first plurality of contact areas; and
  at least one electrical connection being adapted to be utilized solely by the second instrument to auto-calibrate, the at least one electrical connection including at least one contact area, the at least one electrical connection being distinct from the first plurality of electrical connections,
  wherein the first plurality of electrical connections is adapted to be routed directly from each of the first plurality of contact areas to a respective first common connection or a second common connection,
  wherein the at least one electrical connection is adapted to be routed directly from the at least one contact area to the first common connection, the second common connection or a no-contact area.

Alternative Embodiment B

The circuit or label of Alternative Embodiment A wherein the at least one electrical connection includes a second plurality of contact areas, the second plurality of contact areas being distinct from the first plurality of contact areas.

Alternative Embodiment C

The circuit or label of Alternative Embodiment A wherein the first plurality of electrical connections includes a plurality of outer contact areas and the at least one electrical connection includes a plurality of inner contact areas.

Alternative Embodiment D

The circuit or label of Alternative Embodiment C wherein the plurality of outer areas is in a generally radially-extending pattern.

Alternative Embodiment E

The circuit or label of Alternative Embodiment A wherein the first plurality of electrical connections includes a plurality of outer contact areas and the at least one electrical connection includes a plurality of outer periphery contact areas.

Alternative Embodiment F

The circuit or label of Alternative Embodiment A wherein the auto-calibration circuit or label is generally circular shaped.

Alternative Embodiment G

The circuit or label of Alternative Embodiment A wherein the first common connection is an inner ring and the second common connection is an outer ring.

Alternative Embodiment H

The circuit or label of Alternative Embodiment G wherein at least one of the inner ring and the outer ring is continuous.

Alternative Embodiment I

The circuit or label of Alternative Embodiment G wherein the outer ring is continuous.

Alternative Embodiment J

A sensor package adapted to be used in a first instrument adapted to determine an analyte concentration in a fluid sample and in a second instrument adapted to determine the analyte concentration in the fluid sample, the first instrument being different from the second instrument, the sensor package comprising:

at least one sensor being adapted to receive the fluid sample and being operable with the first instrument and the second instrument; and an auto-calibration circuit or label being adapted to be used with the first instrument and the second instrument, the auto-calibration circuit or label including a first plurality of electrical connections and at least one electrical connection, the first plurality of electrical connections being adapted to be utilized by the first instrument to auto-calibrate and being adapted to be utilized by the second instrument to auto-calibrate, the first plurality of electrical connections including a first plurality of contact areas, the at least one electrical connection being adapted to be utilized solely by the second instrument to auto-calibrate, the at least one electrical connection including at least one contact area, the at least one electrical connection being distinct from the first plurality of electrical connections, wherein the first plurality of electrical connections is adapted to be routed directly from each of the first plurality of contact areas to a respective first common connection or a second common connection, wherein the at least one electrical connection is adapted to be routed directly from the at least one contact area to the first common connection, the second common connection or a no-contact area.

Alternative Embodiment K

The sensor package of Alternative Embodiment J further including at least one cavity containing a respective one of the at least one sensor, the at least one cavity being arranged around the auto-calibration label.

Alternative Embodiment L

The sensor package of Alternative Embodiment K wherein the at least one sensor is a plurality of sensors and the at least one cavity is a plurality of cavities, each of the plurality of cavities containing a respective one of the plurality of sensors.

Alternative Embodiment M

The sensor package of Alternative Embodiment J wherein the at least one electrical connection is a second plurality of electrical connections, the second plurality of electrical connections being distinct from the first plurality of electrical connections.

Alternative Embodiment N

The sensor package of Alternative Embodiment J wherein the first plurality of electrical connections includes a plurality of outer contact areas and the at least one electrical connection includes a plurality of inner contact areas.

Alternative Embodiment O

The sensor package of Alternative Embodiment J wherein the first plurality of electrical connections includes a plurality of outer contact areas and the at least one electrical connection includes a plurality of outer periphery contact areas.

Alternative Embodiment P

The sensor package of Alternative Embodiment J wherein the auto-calibration circuit or label is generally circular shaped.

Alternative Embodiment Q

The sensor package of Alternative Embodiment J wherein the first common connection is an inner ring and the second common connection is an outer ring.

Alternative Embodiment R

The sensor package of Alternative Embodiment Q wherein at least one of the inner ring and the outer ring is continuous.

Alternative Embodiment S

The sensor package of Alternative Embodiment Q wherein the outer ring is continuous.

Alternative Embodiment T

The sensor package of Alternative Embodiment J wherein the analyte is glucose.

Alternative Embodiment U

A system for determining an analyte concentration in a fluid sample, the system comprising:

a test sensor being adapted to receive the fluid sample;

a processor responsive to the test sensor and adapted to perform a predefined test sequence for measuring a predefined parameter value; and an auto-calibration circuit or label being coupled to the processor for providing first information and second information corresponding to the test sensor, the processor being adapted to read the first information and second information, the first or second information being utilized by the processor for a predefined test sequence, the second information being defined by a first plurality of electrical connections and at least one electrical connection, the second information being used by the second instrument to auto-calibrate, the first information being defined by the first plurality of electrical connections, the first information being used by the first instrument to auto-calibrate, the first plurality of electrical connections including a first plurality of contact areas, the at least one electrical connection including at least one second contact area, the first plurality of electrical connections being distinct from the at least one electrical connection, wherein the first plurality of electrical connections is adapted to be routed directly from each of the first plurality of contact areas to a respective first common connection or a second common connection, wherein the at least one electrical connection is adapted to be routed directly from the at least one contact area to the first common connection, the second common connection or a no-contact area.

Alternative Embodiment V

The system of Alternative Embodiment U wherein the analyte is glucose.

Alternative Process W

A method of forming an auto-calibration circuit or label adapted to be used with a first instrument and a second instrument, the first instrument being different from the second instrument and adapted to determine an analyte concentration of a fluid sample, the method comprising the acts of:

supplying a first plurality of electrical connections being adapted to be utilized by the first instrument to auto-calibrate and being adapted to be utilized by the second instrument to auto-calibrate, the first plurality of electrical connections including a first plurality of contact areas; and supplying at least one electrical connection being adapted to be utilized solely by the second instrument to auto-calibrate, the at least one electrical connection including at least one contact area, the at least one electrical connection being distinct from the first plurality of electrical connections, wherein the first plurality of electrical connections is adapted to be routed directly from each of the first plurality of contact areas to a respective first common connection or a second common connection, wherein the at least one electrical connection is adapted to be routed directly from the at least one contact area to the first common connection, the second common connection or a no-contact area.

Alternative Process X

The method of Alternative Process W wherein supplying the first plurality of electrical connections includes printing the first plurality of electrical connections and wherein supplying the at least one electrical connection includes printing the at least one electrical connection.

Alternative Process Y

The method of Alternative Process W wherein the at least one electrical connection is a second plurality of electrical connections, the second plurality of electrical connections being distinct from the first plurality of electrical connections.

Alternative Process Z

The method of Alternative Process W wherein the first plurality of electrical connections includes a plurality of outer areas and the at least one electrical connection includes a plurality of inner areas.

While the invention is susceptible to various modifications and alternative forms, specific embodiments are shown by way of example in the drawings and described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

The invention claimed is:

1. An auto-calibration circuit or label adapted to be used with a first instrument and a second instrument, the first instrument being different from the second instrument, the auto-calibration circuit or label comprising:

a first plurality of electrical connections operable by the first instrument to auto-calibrate and operable by the second instrument to auto-calibrate, the first plurality of electrical connections including a first plurality of contact areas; and at least one electrical connection operable solely by the second instrument to auto-calibrate, the at least one electrical connection including at least one contact area, the at least one electrical connection being distinct from the first plurality of electrical connections, wherein the first plurality of electrical connections is operable to be routed directly from each of the first plurality of contact areas to a respective first common connection or a second common connection, wherein the at least one electrical connection is operable to be routed directly from the at least one contact area to the first common connection, the second common connection or a no-contact area.

2. The circuit or label of claim 1, wherein the at least one electrical connection includes a second plurality of contact areas, the second plurality of contact areas being distinct from the first plurality of contact areas.

3. The circuit or label of claim 1, wherein the first plurality of electrical connections includes a plurality of outer contact areas and the at least one electrical connection includes a plurality of inner contact areas.

4. The circuit or label of claim 3, wherein the plurality of outer areas is in a generally radially-extending pattern.

5. The circuit or label of claim 1, wherein the first plurality of electrical connections includes a plurality of outer contact areas and the at least one electrical connection includes a plurality of outer periphery contact areas.

6. The circuit or label of claim 1, wherein the auto-calibration circuit or label is generally circular shaped.

7. The circuit or label of claim 1, wherein the first common connection is an inner ring and the second common connection is an outer ring.

8. The circuit or label of claim 7, wherein at least one of the inner ring and the outer ring is continuous.

9. The circuit or label of claim 7, wherein the outer ring is continuous.

10. A sensor package adapted to be used in a first instrument adapted to determine an analyte concentration in a fluid sample and in a second instrument adapted to determine the analyte concentration in the fluid sample, the first instrument being different from the second instrument, the sensor package comprising:

at least one sensor being operable to receive the fluid sample and being operable with the first instrument and the second instrument; and an auto-calibration circuit or label operable with the first instrument and the second instrument, the auto-calibration circuit or label including a first plurality of electrical connections and at least one electrical connection, the first plurality of electrical connections operable by the first instrument to auto-calibrate and operable by the second instrument to auto-calibrate, the first plurality of electrical connections including a first plurality of contact areas, the at least one electrical connection operable solely by the second instrument to auto-calibrate, the at least one electrical connection including at least one contact area, the at least one electrical connection being distinct from the first plurality of electrical connections, wherein the first plurality of electrical connections is operable to be routed directly from each of the first plurality of contact areas to a respective first common connection or a second common connection, wherein the at least one electrical connection is operable to be routed directly from the at least one contact area to the first common connection, the second common connection or a no-contact area.

11. The sensor package of claim 10, further including at least one cavity containing a respective one of the at least one sensor, the at least one cavity being arranged around the auto-calibration label.

12. The sensor package of claim 11, wherein the at least one sensor is a plurality of sensors and the at least one cavity is a plurality of cavities, each of the plurality of cavities containing a respective one of the plurality of sensors.

13. The sensor package of claim 10, wherein the at least one electrical connection is a second plurality of electrical connections, the second plurality of electrical connections being distinct from the first plurality of electrical connections.

14. The sensor package of claim 10, wherein the first plurality of electrical connections includes a plurality of outer contact areas and the at least one electrical connection includes a plurality of inner contact areas.

15. The sensor package of claim 10, wherein the first plurality of electrical connections includes a plurality of outer contact areas and the at least one electrical connection includes a plurality of outer periphery contact areas.

16. The sensor package of claim 10, wherein the auto-calibration circuit or label is generally circular shaped.

17. The sensor package of claim 10, wherein the first common connection is an inner ring and the second common connection is an outer ring.

18. The sensor package of claim 17, wherein at least one of the inner ring and the outer ring is continuous.

19. The sensor package of claim 17, wherein the outer ring is continuous.

20. The sensor package of claim 10, wherein the analyte is glucose.

21. A system for determining an analyte concentration in a fluid sample, the system comprising:
a test sensor being adapted to receive the fluid sample;
a processor responsive to the test sensor and operable to perform a predefined test sequence for measuring a predefined parameter value; and
an auto-calibration circuit or label being coupled to the processor for providing first information and second information corresponding to the test sensor, the processor being operable to read the first information and second information, the first or second information operable by the processor for a predefined test sequence, the second information being defined by a first plurality of electrical connections and at least one electrical connection, the second information operable by the second instrument to auto-calibrate, the first information being defined by the first plurality of electrical connections, the first information operable by the first instrument to auto-calibrate, the first plurality of electrical connections including a first plurality of contact areas, the at least one electrical connection including at least one second contact area, the first plurality of electrical connections being distinct from the at least one electrical connection,
wherein the first plurality of electrical connections is operable to be routed directly from each of the first plurality of contact areas to a respective first common connection or a second common connection,
wherein the at least one electrical connection is operable to be routed directly from the at least one contact area to the first common connection, the second common connection or a no-contact area.

22. A method of forming an auto-calibration circuit or label adapted to be used with a first instrument and a second instrument, the first instrument being different from the second instrument and adapted to determine an analyte concentration of a fluid sample, the method comprising the acts of:
supplying a first plurality of electrical connections being adapted to be utilized by the first instrument to auto-calibrate and being adapted to be utilized by the second instrument to auto-calibrate, the first plurality of electrical connections including a first plurality of contact areas; and
supplying at least one electrical connection being adapted to be utilized solely by the second instrument to auto-calibrate, the at least one electrical connection including at least one contact area, the at least one electrical connection being distinct from the first plurality of electrical connections,
wherein the first plurality of electrical connections is adapted to be routed directly from each of the first plurality of contact areas to a respective first common connection or a second common connection,
wherein the at least one electrical connection is adapted to be routed directly from the at least one contact area to the first common connection, the second common connection or a no-contact area.

23. The method of claim 22, wherein supplying the first plurality of electrical connections includes printing the first plurality of electrical connections and wherein supplying the at least one electrical connection includes printing the at least one electrical connection.

24. The method of claim 22, wherein the at least one electrical connection is a second plurality of electrical connections, the second plurality of electrical connections being distinct from the first plurality of electrical connections.

25. The method of claim 22, wherein the first plurality of electrical connections includes a plurality of outer areas and the at least one electrical connection includes a plurality of inner areas.

* * * * *